US00PP14106P39

(12) United States Plant Patent
Kordes

(10) Patent No.: US PP14,106 P3
(45) Date of Patent: Aug. 26, 2003

(54) MINIATURE ROSE PLANT NAMED 'KORJUBLA'

(75) Inventor: Tim-Hermann Kordes, Offenseth-Sparrieshoop (DE)

(73) Assignee: W. Kordes Sohne Rosenschulen GmbH & Co. KG (DE)

( * ) Notice: Subject to any disclaimer, the term of this patent is extended or adjusted under 35 U.S.C. 154(b) by 0 days.

(21) Appl. No.: 10/045,879

(22) Filed: Nov. 7, 2001

(65) Prior Publication Data

US 2003/0088894 P1 May 8, 2003

(51) Int. Cl.[7] ..... A01H 5/00

(52) U.S. Cl. ..... Plt./119

(58) Field of Search ..... Plt./119

*Primary Examiner*—Bruce R. Campell
*Assistant Examiner*—W C Haas
(74) *Attorney, Agent, or Firm*—Webb Ziesenhiem Logsdon Orkin & Hanson, P.C.

(57) ABSTRACT

A new miniature rose plant which has abundant, orange-yellow colored flowers and attractive glossy dark foliage. The variety successfully propagates from softwood cuttings and is suitable for year round production in commercial glasshouses as a flowering pot plant.

3 Drawing Sheets

Botanical classification: Rosa hybrida.
Varietal denomination: 'KORjubla'.

BACKGROUND OF THE NEW PLANT

The present invention constitutes a new and distinct variety of miniature rose plant named 'KORjubla' which was developed by artificially pollinating an unnamed seedling (unpatented) with an unnamed seedling (unpatented).

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'KORjubla' from other varieties.

The two parents were crossed in the summer of 1999 and the resulting seed was sown in December 1999 in a controlled glasshouse environment. The seeds from hybridization were planted in a controlled environment in Klein Offenseth, Sparrieshoop, Germany and evaluations were conducted on the resulting plants.

Asexual reproduction of 'KORjubla' by softwood cuttings was first done in Denmark and later in California in controlled greenhouse environments. The characteristics of the new variety remain as true to type through successive propagations.

The new rose variety may be distinguished from its seed parent, an unnamed breeding seedling, by the following combination of characteristics:

1. 'KORjubla' has big double flowers, while the seed parent has big single flowers.

2. 'KORjubla' has orange-yellow colored petals, while the seed parent has dark yellow petals.

The new variety may be distinguished from its pollen parent, an unnamed breeding seedling by the following combination of characteristics:

1. 'KORjubla' has smaller flowers and foliage as compared to the pollen parent.
2. 'KORjubla' has Orange-Yellow colored petals, while the pollen parent has light yellow petals.

The new variety differs from 'KORbritta', U.S. Plant Pat. No. 11,146, as set forth in Table 1.

TABLE 1

| | 'KORjubla' | 'KORbritta' |
|---|---|---|
| Petal color, upper surface | Orange Group 24A–B | Yellow-Orange Group 21B |
| Petal color, reverse surface | Orange Group 29A | Yellow-Orange Group 21B |
| Petal count | 35–45 petals | 20–25 petals |

DESCRIPTION OF THE DRAWINGS

The accompanying color illustrations show as true as is reasonably to obtain in color photographs of this type, the typical characteristics of the buds, flowers, leaves, stems of 'KORjubla'.

In photo sheet # 1.

Figures 1, 2, 3, 4, 5, 6, 7, 8, 9:
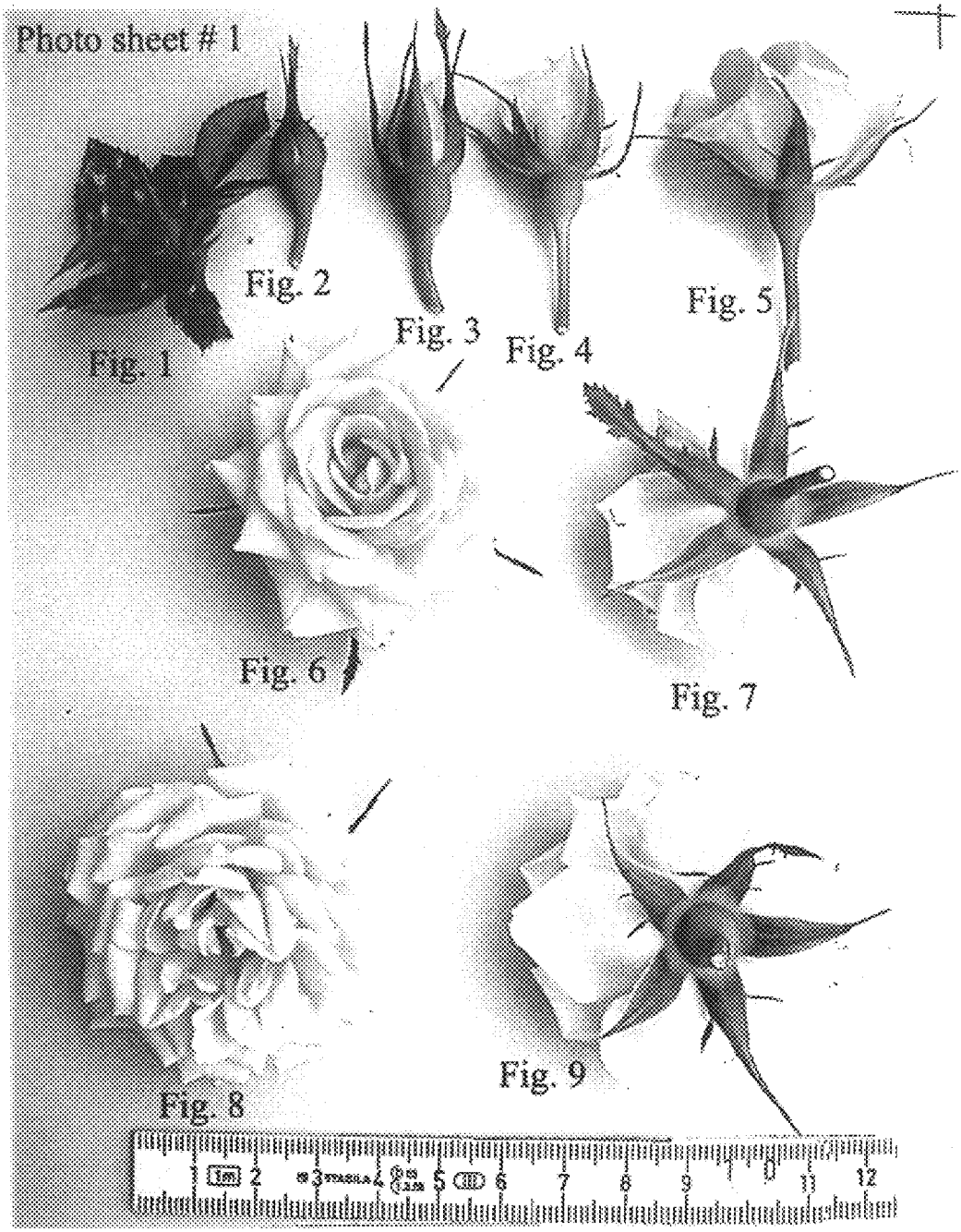
FIG. 1 shows a young shoot.
FIG. 2 shows a bud before opening of the sepals.
FIG. 3 shows a bud at the opening of the sepals.
FIG. 4 shows a bud at the opening of the petals.
FIG. 5 shows a flower during the course of opening.
FIG. 6 shows an open flower, obverse plan view.
FIG. 7 shows an open flower, reverse plan view.
FIG. 8 shows a fully open flower, obverse plan view.
FIG. 9 shows a fully open flower, reverse plan view.
Figures 10, 11, 12, 13, 14, 14A:
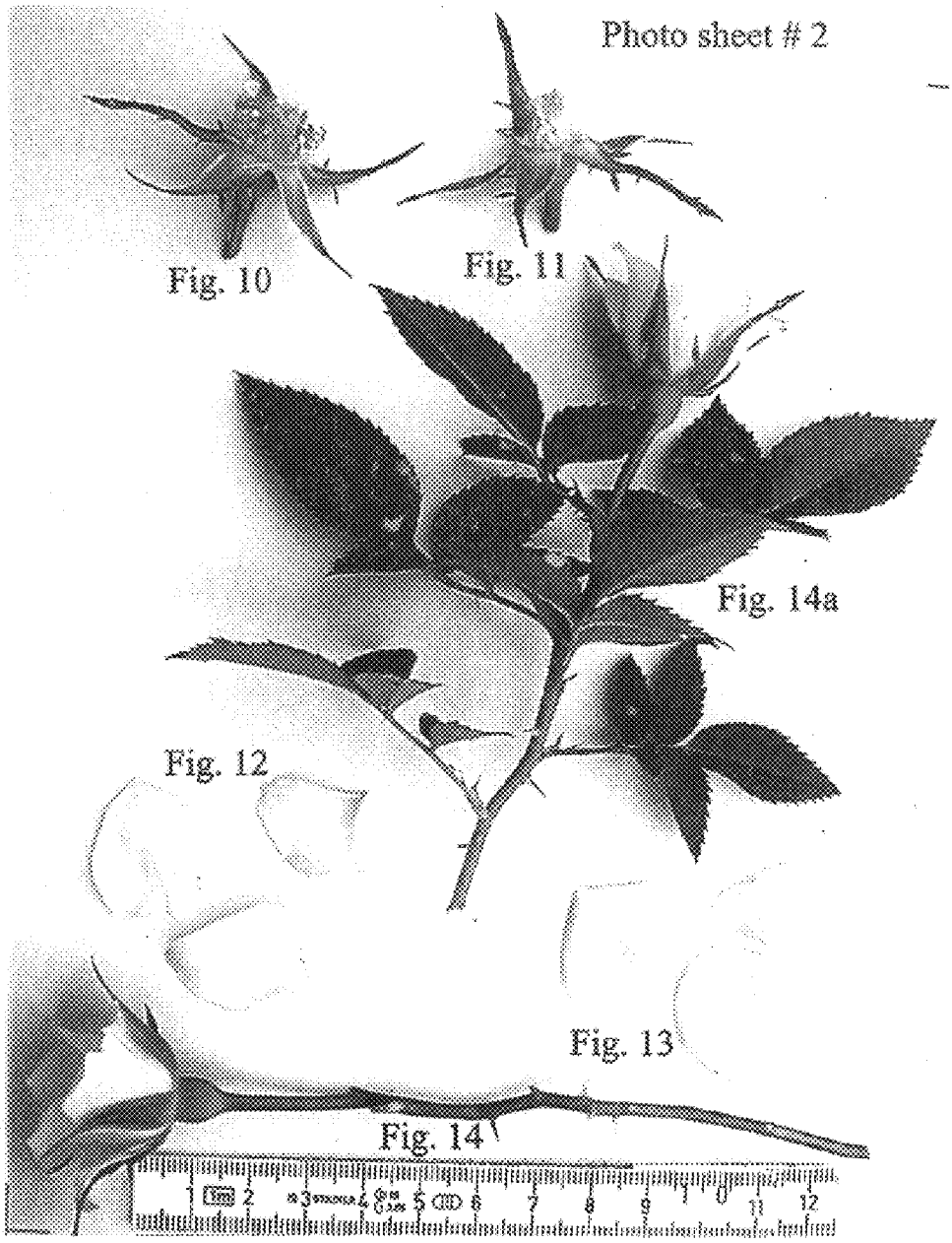

In photo sheet # 2:

FIG. 10 shows a receptacle with stamens and pistils.

FIG. 11 shows a receptacle with pistils and stamens removed.

FIG. 12 shows detached flower petals, outer surface.

FIG. 13 shows detached flower petals, inner surface.

FIG. 14 shows a bare stem exhibiting thorns and flower attachment.

In photo sheet #3:

FIG. 15 shows three leaflets, upper side.

FIG. 16 shows three leaflets, under side.

FIG. 17 shows five leaflets, upper side.

FIG. 18 shows five leaflets, under side.

DESCRIPTION OF THE NEW PLANT

The following is a detailed description of 'KORjubla', as observed in its growth in greenhouses in Fraugde, Denmark and greenhouses in Santa Barbara Calif., both at 20–25° C.

Descriptions were made from plants 11 to 13 weeks old after propagation, produced in a pot treated with growth regulators normally used in the greenhouse production process. The growth regulator Paclobutrazol was applied at 15–30 ppm weekly beginning at a plant age of 8 weeks. The peduncle lengths mentioned may actually be shorter and the foliage color several shades darker than on untreated specimens. Color references are made using The Royal Horticultural Society (London, England) Colour Chart, 1995, except where common terms of color are used.

THE PLANT

Classification:
- *Botanical.*—Rosa hybrida.
- *Commercial.*—Miniature.

Plant growth: Moderately vigorous. Grows compact upright to bushy. When grown as 10 cm pot plant, the average height of the plant itself is 18–20 cm, and average width is 20 cm. When grown as a 15 cm pot plant, the average height of the plant itself is 22–27 cm, and average width is 30 cm. Production time is generally 11–13 weeks depending on average temperature, light level, and cultural practices.

Stem:
- *Color.*—Young wood: Green Group 138B, with intonations of Greyed-Red Group 178A–B. Older wood: Green Group 138A.
- *Surface.*—Young wood: Smooth. Older wood: Smooth.
- *Stem diameter.*—2–5 mm.
- *Internode length.*—10–25 mm.
- *Number of internodes.*—7–10.
- *Thorns.*—Incidence: Moderate number of thorns. Size: 5–6 mm.
- *Color.*—Young: Red-Purple Group 66C. Mature: Greyed-Orange Group 165C–D.
- *Shape.*—Hooked downwards.

FOLIAGE

Arrangement: Alternate, compound with 3–7 leaflets per leaf, generally symmetrical, abundant, and flat in aspect. Stipules at petiole base.

Quantity of leaves: 7–10 per lateral branch.

Leaf size:
- *Length.*—70–85 mm.
- *Width.*—55–65 mm.

Petioles:
- *Color.*—Green Group 138C with intonations of Green Group 136B on upper surface.
- *Prickles.*—On lower surface.
- *Length.*—10–15 mm.
- *Diameter.*—About 1 mm.

Stipules:
- *Size.*—8–10 mm.
- *Surface.*—Smooth.
- *Color.*—Green Group 137B with intonations of Red-Purple Group 66B.
- *Margin.*—Stipitate glands present.

Rachis:
- *Color.*—Green Group 137B with intonations of Greyed-Red Group 185A.
- *Prickles.*—On lower surface.
- *Length.*—10–25 mm.

Leaflets:
- *Margin.*—Serrated.
- *Shape.*—Ovate with acute apex and obtuse base.
- *Texture.*—Smooth.
- *Appearance.*—Glossy.
- *Size.*—Length: 15–45 mm. Width: 15–20 mm.
- *Color.*—Young foliage: Upper surface: Green Group 137A. Lower surface: Green Group 138A. Mature foliage: Upper surface: Green Group 139A. Lower surface: Yellow-Green Group 138A.

INFLORESCENCE

Blooming habit: Recurrent.

Number of flowers: Generally 1–3 buds per flowering stem.

Peduncle:
- *Color.*—Green Group 138A with intonations of Greyed-Red Group 178A–B.
- *Texture.*—Smooth.
- *Length.*—20–25 mm.
- *Form.*—Upright.
- *Receptacle.*—Surface: Smooth. Shape: Funnel-shaped. Size: Height: 7 mm. Width: 8 mm.
- *Color.*—Green Group 138A with intonations of Greyed-Red Group 178A–B.

Sepals:
- *Quantity.*—5.
- *Shape.*—Narrowly ovate with acute tip.
- *Texture.*—Slightly pubescent.
- *Margin.*—Foliaceous appendages on three of the five sepals.
- *Appearance.*—Dull.
- *Color.*—Upper surface: Green Group 138A. Reverse surface: Green Group 138B–D.

Buds:
- *Size when just opening.*—Length: 20–25 mm. Width: 12–14 mm.
- *Shape.*—Ovoid.
- *Color.*—Orange Group 25B–C at one-fourth opened.

Flower:
- *Duration.*—As a pot plant, flowers last 10–16 days.
- *Fragrance.*—None.
- *Size.*—45–50 mm in diameter on average.
- *Form* (*shape of flower when viewed from the side*).—Upon opening:Cupped. Open flower: Flat.
- *Color.*—Petals, upon opening: Upper surface: Orange Group 24A, with intonations of Yellow Group 13A toward the basal petal spots. Reverse surface: Orange Group 29A, with intonations of Yellow Group 13A toward the basal petal spots. Petals, after opening: Upper surface: Yellow Group 11D, with intonations of Yellow Group 13A toward basal petal spots. Reverse surface: Yellow Group 11D, with intonations of Yellow Group 13A toward basal petal spots. Basal petal spots: Size: 5–10 mm. Color: Green-White Group 157D to Yellow Group 11C. General tonality of open flower: Orange Group 24A–B on third day fading to Yellow-Orange Group 19A–B.

Petals:

*Petal reflex.*—Outermost petals reflex backwards upon opening. Fully open, all petals reflex backward.

*Texture.*—Smooth and satiny.

*Petal edge.*—Uniform.

*Petal count.*—Approximately 35–45 per flower.

*Petal size.*—Length: 25 mm. Width: 20 mm.

*Shape.*—Outer petals: Ovate to round. Inner petals: Ovate to round.

*Petaloids.*—Usually none.

Reproductive organs:

*Stamens.*—Number: Approximately 80–90 per flower. Pollen: Color: Greyed-Orange Group 164A. Amount: Average. Anthers: Size: 1 mm. Color: Greyed-Orange Group 164A. Shape: Oblong. Number: 80–90. Filaments: Size: 3–4 mm. Color: Yellow-Green Group 154D.

*Pistils.*—Number: Approximately 50–60 per flower. Stigmas: Location: Superior in location to anthers. Color: Yellow Group 1C. Styles: Color: Yellow Group 1C. Length: 2–3 mm.

GROWTH

Vegetation: Dense.

Blooming: Abundant.

Aptitude to bear fruit: Poor.

Resistance to diseases: Above average resistance to mildew and Botrytis under normal growing conditions in Fraugde, Denmark and Santa Barbara, Calif.

Hips/seeds: Unknown because the plant has not been grown to the stage of seed development due to the fact that the variety is developed for use as a flowering potted plant only.

Winter hardiness and drought/heat tolerance: This variety is a potted flowering plant developed for one time use only and has not been tested for winter hardiness or drought/heat tolerance.

I claim:

1. A new and distinct variety of rose plant substantially as shown and described.

* * * * *

Photo sheet # 1

Photo sheet # 2

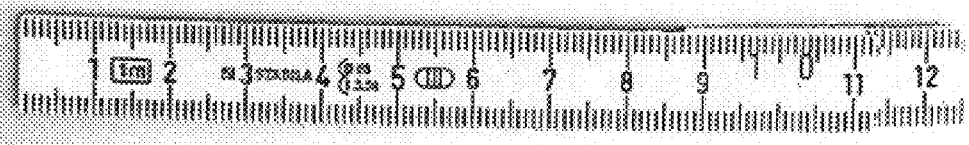

Phototsheet # 3
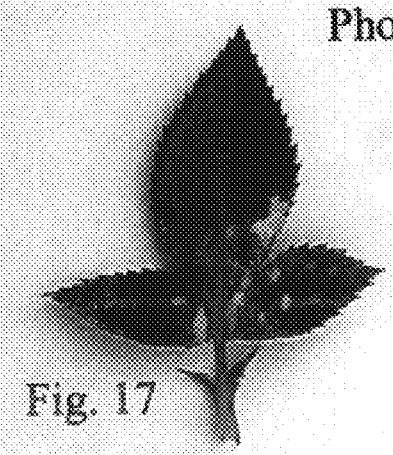
Fig. 17
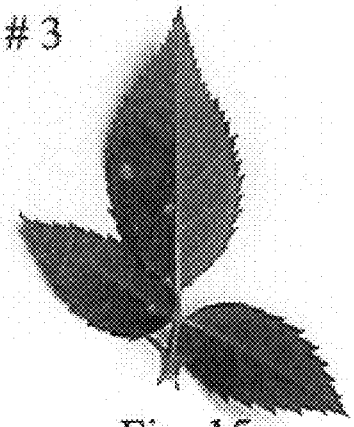
Fig. 15
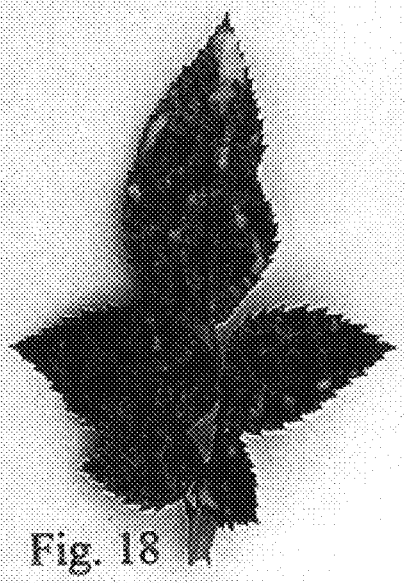
Fig. 18
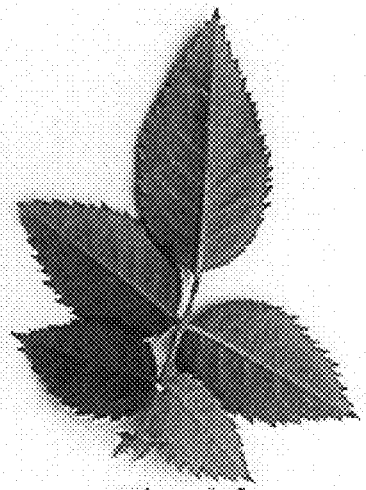
Fig. 16